United States Patent
Lee

(10) Patent No.: US 9,486,629 B2
(45) Date of Patent: Nov. 8, 2016

(54) BRAIN STIMULATING SYSTEM

(71) Applicant: YBRAIN INC., Seoul (KR)

(72) Inventor: Kiwon Lee, Seoul (KR)

(73) Assignee: YBRAIN INC., Seoul (KR)

( * ) Notice: Subject to any disclaimer, the term of this patent is extended or adjusted under 35 U.S.C. 154(b) by 40 days.

(21) Appl. No.: 14/104,501

(22) Filed: Dec. 12, 2013

(65) Prior Publication Data

US 2015/0148863 A1    May 28, 2015

(30) Foreign Application Priority Data

Nov. 25, 2013  (KR) .................. 10-2013-0144087

(51) Int. Cl.
| | | |
|---|---|---|
| *A61N 1/00* | (2006.01) | |
| *A61N 1/36* | (2006.01) | |
| *A61B 5/0484* | (2006.01) | |
| *A61N 1/04* | (2006.01) | |
| *A61B 5/04* | (2006.01) | |
| *A61B 5/0478* | (2006.01) | |
| *A61N 1/372* | (2006.01) | |
| *A61B 5/00* | (2006.01) | |
| *A61N 1/05* | (2006.01) | |

(52) U.S. Cl.
CPC ....... *A61N 1/36025* (2013.01); *A61B 5/04001* (2013.01); *A61B 5/0478* (2013.01); *A61B 5/0484* (2013.01); *A61B 5/4064* (2013.01); *A61B 5/6868* (2013.01); *A61B 5/7225* (2013.01); *A61N 1/0456* (2013.01); *A61B 5/0006* (2013.01); *A61B 5/7217* (2013.01); *A61N 1/0526* (2013.01); *A61N 1/37282* (2013.01)

(58) Field of Classification Search
CPC .................... A61N 1/0529; A61N 1/0531
USPC ............................................... 607/45
See application file for complete search history.

(56) References Cited

U.S. PATENT DOCUMENTS

| | | | | |
|---|---|---|---|---|
| 5,205,297 | A | * | 4/1993 | Montecalvo et al. ........ 607/152 |
| 2008/0021514 | A1 | * | 1/2008 | Pless ............................ 607/45 |
| 2008/0045850 | A1 | * | 2/2008 | Phillips ...................... 600/509 |
| 2011/0137381 | A1 | * | 6/2011 | Lee et al. ..................... 607/62 |
| 2011/0288610 | A1 | | 11/2011 | Brocke |
| 2012/0296390 | A1 | | 11/2012 | Nakashima et al. |
| 2013/0079659 | A1 | | 3/2013 | Akhadov et al. |

FOREIGN PATENT DOCUMENTS

| | | |
|---|---|---|
| JP | 2010516329 A | 5/2010 |
| JP | 2012520730 A | 9/2012 |
| JP | 2012239696 A | 12/2012 |
| JP | 2013507174 A | 3/2013 |
| KR | 1020030002677 | 1/2003 |
| KR | 1020100014815 | 2/2010 |
| KR | 101094350 | 12/2011 |

* cited by examiner

*Primary Examiner* — Christopher D Koharski
*Assistant Examiner* — Philip C Edwards
(74) *Attorney, Agent, or Firm* — Hauptman Ham, LLP

(57) ABSTRACT

A brain stimulating system is provided. In some embodiments, the system includes a first electrode configured to supply a minute electric current to stimulate a brain, and a second electrode configured to detect at least one brain signal received from a brain, wherein the second electrode includes a blocking filter configured to block the minute electric current.

21 Claims, 12 Drawing Sheets

BRAIN STIMULATING SYSTEM

CROSS-REFERENCE TO RELATED APPLICATION

This application claims the priority of the Korean Patent Application No. 10-2013-0144087 filed on Nov. 25, 2013 in the Korean Intellectual Property Office, and all the benefits accruing therefrom under 35 U.S.C. §119, the contents of which in their entirety are herein incorporated by reference.

TECHNICAL FIELD

The present disclosure relates to a brain stimulating system.

The brain, an internal organ in a head of a human body, is the supreme and vital organ of the nervous system, and includes a cerebrum, cerebellum, midbrain, pons and medulla oblongata. Furthermore, the brain generates electroencephalograms, or brain signals, signals measured at the epidermis of the brain, which is the sum of activation levels of neurons.

Measurements of the brain comprise EEG (electroencephalogram) that scans and measures electroencephalograms received from electrodes on a pad installed on a scalp, CT (computed tomography) that scans and measures the brain using radiation or ultrasound to perform a tomographic scan from various viewpoints, and MRI (magnetic resonance imaging) that scans the brain exploiting the property of nuclear magnetic resonance, and so on.

A number of concepts are known to the field of nerve stimulation of brain structures, and brain stimulation generally consists of invasive brain stimulation and non-invasive brain stimulation.

Invasive brain stimulation is a method that inserts electrodes into the brain by surgery and delivers electric signals, and non-invasive brain stimulation is a method that stimulates the brain not inserting electrodes within the cranium and thus accomplishing an anticipated end.

In detail, brain stimulation includes a deep electrical stimulation, TMS (transcranial magnetic stimulation) and TES (transcranial electrical stimulation), particularly tDCS (transcranial direct current stimulation) and tRNS (transcranial random noise stimulation).

In the case of tDCS, particularly, a weak direct current is continuously applied through two touching electrodes on the scalp. This causes fine alterations in membrane potential and changes in firing rate of cortical nerve cells, thus influencing an excitement level of the cortical nerve cells. To be more specific, the excitement level increases or decreases depending on a polarity of the electrodes. In the case of stimulating an anode (the anode is in the neighborhood of the cell body or dendrite of the cortical nerve cells), depolarization takes place by an increased membrane potential and firing rate, thus augmenting the excitement of the cortical nerve cells. In the case of stimulating a cathode, nerve cells become hyperpolarized as a result of the decreased membrane potential and firing rate.

SUMMARY

In accordance with some embodiments, there is provided a brain stimulating system, the system comprising a first electrode configured to supply a minute electric current to stimulate a brain, and a second electrode configured to detect at least one brain signal received from the brain, wherein the second electrode comprises a blocking filter configured to block the minute electric current.

In accordance with some embodiments, there is provided a brain stimulating system, the system comprising a first electrode configured to supply a minute electric current to stimulate a brain, and detect at least one brain signal received from the brain, a stimulating element configured to control the minute electric current, the stimulating element connected with the first electrode, and a detecting element configured to receive the at least one brain signal, the detecting element connected with the first electrode, wherein the detecting element comprises a blocking filter configured to block the minute electric current.

In accordance with some embodiments, there is provided a brain stimulating system, the system, the system comprising a first device comprising a stimulating element configured to generate a minute electric current to stimulate a brain and a detecting element configured to measure at least one brain signal received from the brain, and a second device comprising a control unit configured to receive data containing the at least one brain signal from the first device and manage the received data.

DETAILED DESCRIPTION

A brain stimulating system will be described more fully hereinafter with reference to the accompanying drawings, in which some embodiments are shown. Advantages and features of some embodiments accomplishing the same are hereafter detailed with reference to the accompanying drawings. The brain stimulating system is embodied in different forms and should not be construed as limited to the embodiments set forth herein. Rather, these embodiments are provided so that this disclosure will be thorough and complete, and will fully convey the scope of the brain stimulating system to those skilled in the art. The same reference numbers indicate the same components throughout the specification.

Unless defined otherwise, all technical and scientific terms used herein have the same meaning as commonly understood by one of ordinary skill in the art to which this application belongs. It is noted that the use of any and all examples, or exemplary terms provided herein is intended merely to better illuminate the brain stimulating system and is not a limitation on the scope of the brain stimulating system unless otherwise specified. Further, unless defined otherwise, all terms defined in generally used dictionaries may not be overly interpreted.

The use of the terms "a" and "an" and "the" and similar referents in the context of describing the brain stimulating system (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

A detailed description of the brain stimulating system is hereafter presented with reference to the accompanying drawings.

Figure 1:
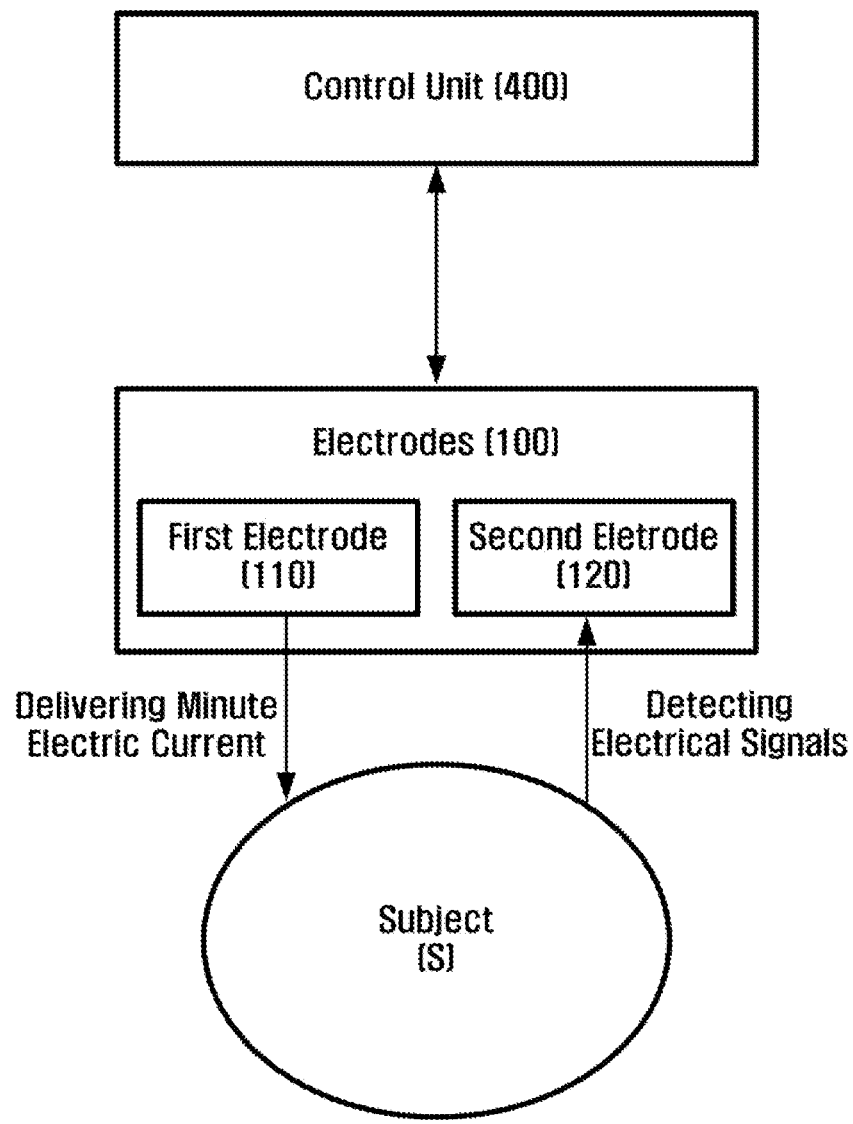
FIG. 1 is a schematic block diagram of a brain stimulating system according to some embodiments.

FIG. 1 is a schematic block diagram of a brain stimulating system according to some embodiments. The brain stimulating system in some embodiments includes electrodes 100 and a control unit 400, and the electrodes 100 include a first electrode 110 and a second electrode 120, either connected or disconnected with the first electrode 110, that detects the brain signal received from the brain. The first electrode 110 supplies supply a minute electric current to stimulate the brain, and the second electrode 120 detects at least one brain signal. In some embodiments, the second electrode 120 detects a plurality of brain signals. In some embodiments, the second electrode 120 detects at least one brain signal in response to the supplied minute electric current. In another some embodiments, the first electrode 110 supplies the minute electric current in response to the detected at least one brain signal. That is, the order of detecting and supplying is changed according to some embodiments.

The electrodes 100 are arranged at a head of a subject S. In some embodiments, the first electrode 110 and the second electrode 120 are arranged at a frontal lobe area of the head of the subject. In some embodiments, the electrodes 100 comprise contact electrodes which directly contact with a scalp or skin of the head of the subject. The electrodes 100 also comprise a circuit and a power supply which deliver electrical signals to the contact electrodes or receiving electrical signals from the contact electrodes.

The second electrode 120 which detects at least one brain signal from the subject S needs not adhere to the subject's skin, for instance, the frontal lobe area of the scalp. In some embodiments, the second electrode 120 detects the brain signal, even when the second electrode 120 is separated from the skin, by using an air layer between the skin and the second electrode 120 as a capacitor layer.

The second electrode 120 detects the brain signal corresponding to states of the brain, and the second electrode 120 detects brain signals generated from the brain, wherein the brain signals include various kinds of signals besides electrical signals. For example, signals from the brain are detected by a variety of ways such as ultrasound or MRI. In some embodiment, the second electrode 120 comprises one or more modules needed to detect each of signals of the variety of ways, and the second electrode 120 is constituted as a non-contact form which is not directly contacting with the scalp.

In some embodiments, brain signals received from the second electrode 120 include, for example, electroencephalogram (EEG), near-infrared signals, impedance signals, acoustic signals, magnetic signals, mechanical signals, chemical signals, optical signals, ultrasonic signals, and so forth.

In some embodiments, the first electrode 110 is adhered to the scalp of the subject S if a minute electric current is directly supplied as in a case of transcranial direct current stimulation (tDCS), but the first electrode 110 does not need to be adhered to the scalp of the subject S if the minute electric current is supplied to the frontal lobe area of the scalp through means such as transcranial magnetic stimulation (TMS). The minute electric current is at least one of a micro current or a small amount of current, which is less than a predetermined amperes according to setting of the brain stimulating system. In some embodiments, the minute electric current is a milliampere (mA) current, which is one-digit milliampere.

There is no limit to materials for the electrodes 100, and in some embodiments, the electrodes 100 includes metallic conductors or non-metallic materials. Each of the first electrode 110 and the second electrode 120 is comprised of a plural number of electrodes. In some embodiments, the each of the first electrode 110 and the second electrode 120 is fixed at a first device 500 of FIG. 9 so that the each of the first electrode 110 and the second electrode 120 is located in a place wherein, when the first device 500 is worn on a transcranial area of the subject S, the each of the first electrode 110 and the second electrode 120 is located for applying electric stimulation to at least one of a dorsolateral prefrontal cortex, ventromedial prefrontal cortex, primary motor cortex, temporal lobe and occipital lobe.

The electrodes 100, in addition to the first electrode 110 which supplies the minute electric current and the second electrode 120 which detects the at least one brain signal from the subject S, further comprises a third electrode (not shown in FIG. 1) for the purpose of noise removal and increase of accuracy of a brain signal detection considering a reference current.

The control unit 400 receives at least one brain signal sent from the electrodes 100, and either generates and outputs at least one electric stimulating signal with a plurality of electrodes attached to a certain location of the transcranial area in response to a frequency of the brain signal, or generates and outputs at least one signal that actuates a brain signal sensor to detect brain signals at a certain location of the transcranial area.

In some embodiments, the control unit 400 is constituted with a transformer, one or more frequency filters, and one or more rectifying elements. The transformer transforms a voltage sent from the electrodes 100 by a predetermined ratio and outputs the transformed voltage. The one or more frequency filters distinctively receive each electrical signal sent from the transformer, which has different passbands from each other, and then pass or block electrical signals in response to the each frequency value of the each electrical signal. The one or more rectifying elements respond to the one or more frequency filters respectively and are electrically connected. In some embodiments, the one or more rectifying elements concurrently rectify the electrical signals passed from the frequency filters electrically connected with the electrodes 100 and output the rectified electrical signals.

If the electrical rectified signals are output from the one or more rectifying elements electrically connected with the electrodes 100, the rectified electrical signals work by actuating signals of an amplifying element (not shown in FIG. 1), and brain signals detected from detecting electrodes (not shown in FIG. 1) that detect brain signals at a certain location of the transcranial area are amplified and output.

A control unit 400 analyzes brain signals received from the second electrode 120 that constitutes electrodes 100 so as to analyze a current status of the subject S, and determines an optimal range of stimulation for the subject S and delivers a control instruction that reflects a range to the first electrode 110. The first electrode 110, which receives the control instruction, generates the minute electric current responding to an optimal range of stimulation, thus accomplishing an anticipated end.

In some embodiments, the control unit 400 delivers one or more control signals for generating and putting out electrical signals having predetermined frequency value according to chosen signals by a user to the first electrode 110.

The chosen signals by the user indicate the user's choice of what signal stimulation will be performed among various electrical signals, or the chosen signals mean signals that indicate user's choice of whether a brain signal detection is performed via the second electrode 120, and according to the user's choice, one or more frequency values are predetermined.

In some embodiments, the control unit 400 is electrically connected with electrodes 100, or in some other embodiments, the control unit 400 is separately arranged from the electrodes 100, and the control unit 400 is a composition contained to another device.

The control unit 400 includes one or more physical, actual storage devices. Examples of physical, actual storage devices include, but are not limited to, magnetic media such as, a hard disk, a floppy disk, and a magnetic tape, optical media such as a CD-ROM and a DVD, magneto-optical media such as a floptical disk, and a hardware device configured especially to store and execute a program, such as a ROM, a RAM, a solid state drive, and a flash memory. The control unit 400 is implemented by one or more programmed processors and/or application-specific integrated circuits (ASICs).

Figure 2:
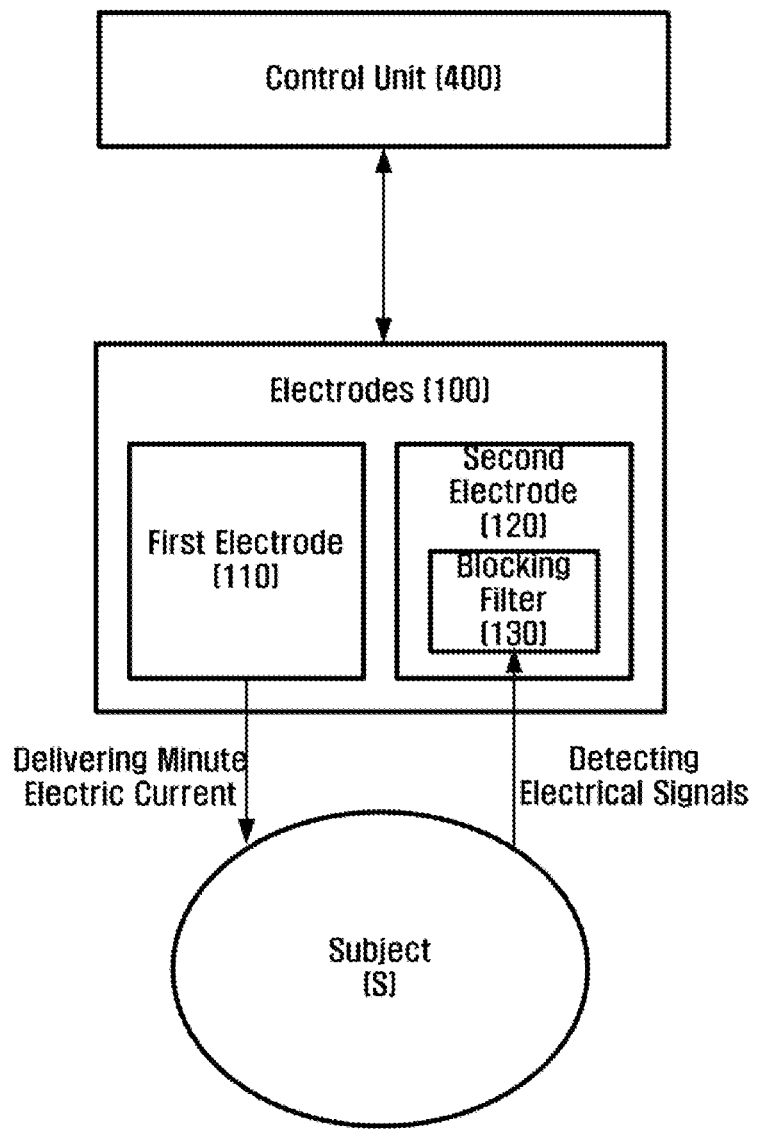
FIG. 2 is a schematic block diagram of the system of FIG. 1, which further comprises a blocking filter, according to some embodiments.

FIG. 2 is a schematic block diagram of the system of FIG. 1, which further comprises a blocking filter, according to some embodiments. With reference to FIG. 2, in electrodes 100, a second electrode 120 further contains a blocking filter 130 that blocks an electric current. In the case in which a first electrode 110 supplies a minute electric current to a frontal lobe area of a brain, while the first electrode 110 and the second electrode share an electrode or are closely arranged to each other, the supplied minute electric current is, in entirety, detected at the second electrode 120, and if so, a control unit 400 have difficulty for analyzing brain signals in an accurate way.

Therefore, a blocking filter 130 is equipped at a frontal part of the second electrode 120 so that the minute electric current supplied from the first electrode 110 is shut off, thus brain signal information, being distorted, is not supplied to the control unit 400. The blocking filter 120 blocks the minute electric current.

In some embodiments, the minute electric current generated from the first electrode 110 to stimulate the frontal lobe area by using tDCS is a direct current (DC), whereas brain signals received from the second electrode 120 is an alternating current (AC). Therefore, in some embodiments, the blocking filter 130 is constituted as a DC blocking filter and is arranged at the frontal part of the second electrode 120.

Figure 3:
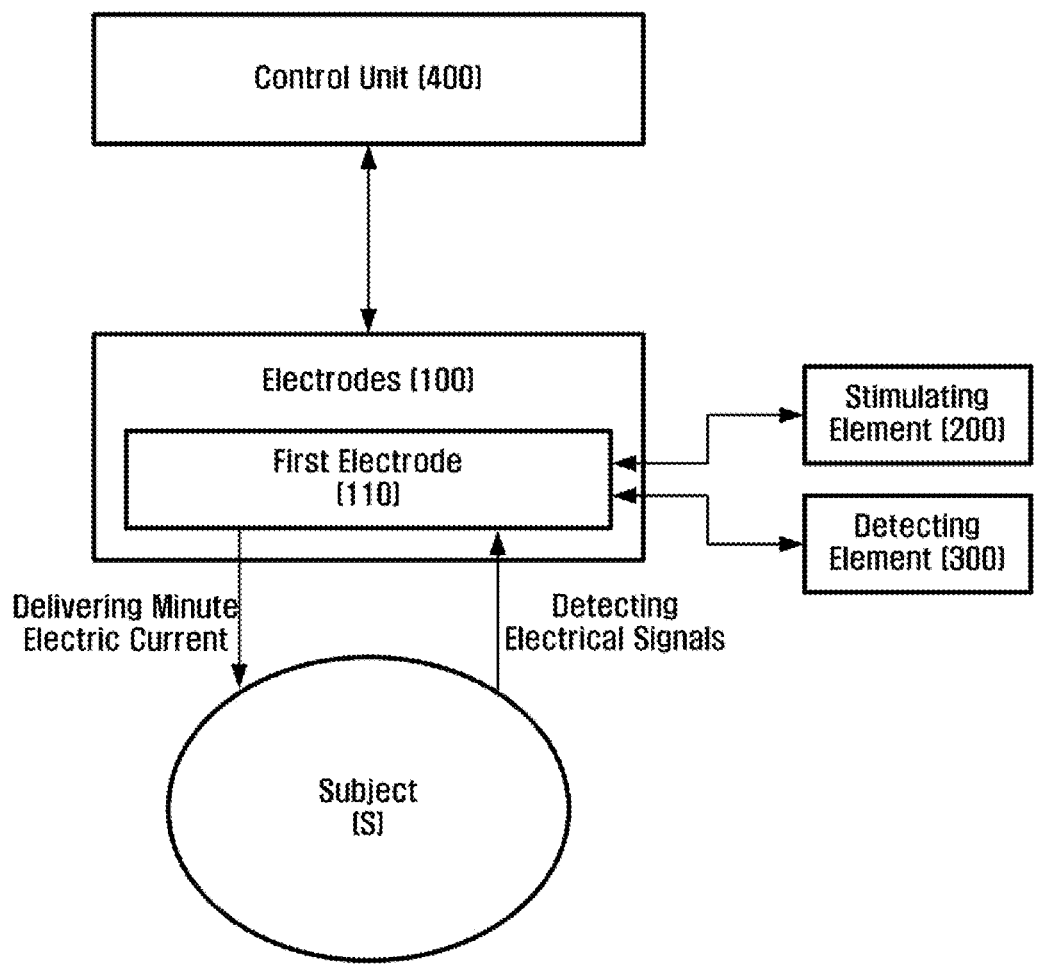
FIG. 3 is a schematic block diagram of a brain stimulating system according to some embodiments.
Figure 4:
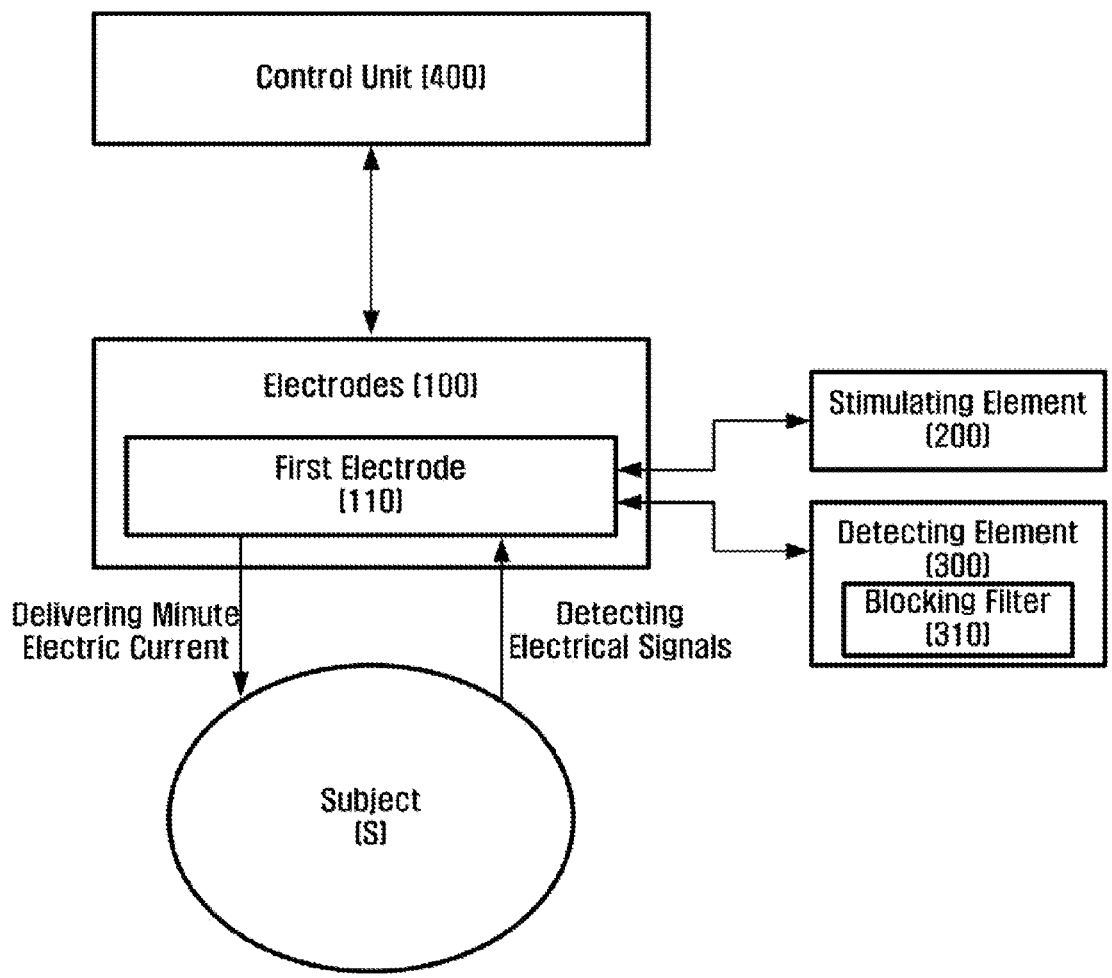
FIG. 4 is a schematic block diagram of the system of FIG. 3, which further comprises a blocking filter, according to some embodiments.

FIG. 3 is a schematic block diagram of a brain stimulating system, according to some embodiments, and FIG. 4 is a schematic block diagram of the system of FIG. 3, which further comprises a blocking filter, according to some embodiments. Referring to FIGS. 3 and 4, the brain stimulating system conforming to some another embodiments is disclosed. The brain stimulating system according to these some another embodiment, electrodes 100 comprise one electrode, which is, a first electrode 110, and a stimulating element 200 and a detecting element 300 share the first electrode 110.

In other words, the first electrode 110 delivers a minute electric current or detects at least one brain signal received from the brain. The stimulating element 200, connected with the first electrode 110, controls the minute electric current. The detecting element 300, connected with the first electrode 110, receives the brain signal detected from a subject S.

Like the aforementioned embodiments, the system further comprises a blocking filter 310 that blocks the minute electric current supplied to the subject S via the first electrode 110 and prevents data from a distortion. The blocking filter 310 is equipped at a frontal part of the detecting element 300 that detects the at least one brain signal so that a distorted brain signal received directly through the detecting element 300 as electric current delivered from the stimulating element 200 are not sent to a control unit 400. Therefore, in some embodiments, the blocking filter 310 is constituted as a DC blocking filter and is arranged at the frontal part of the detecting element 300.

In some embodiments, the stimulating element 200 comprises a high voltage module, a stabilization module, a limitation module, an output module, or a current/voltage measurement module. The stimulating element 200 provides signals to user's brain, thus stimulating the brain's certain area, and in some embodiments, the stimulating element 200 actuates functions of certain area of the brain. The stimulating element 200 also blocks an electric current by means of a current/voltage measurement module so that an excessive current is not delivered to a scalp of the subject S.

In some embodiments, the detecting element 300 comprises the blocking filter 310, a noise processing module, an amplifying module, or an anti-phase noise output module. The detecting element 300 collects brain signals detected from the brain, and removes one or more noise signals besides one or more brain signals or performs an anti-phase neutralization process by separating a noise flowing on a surface of the scalp.

Figure 13:
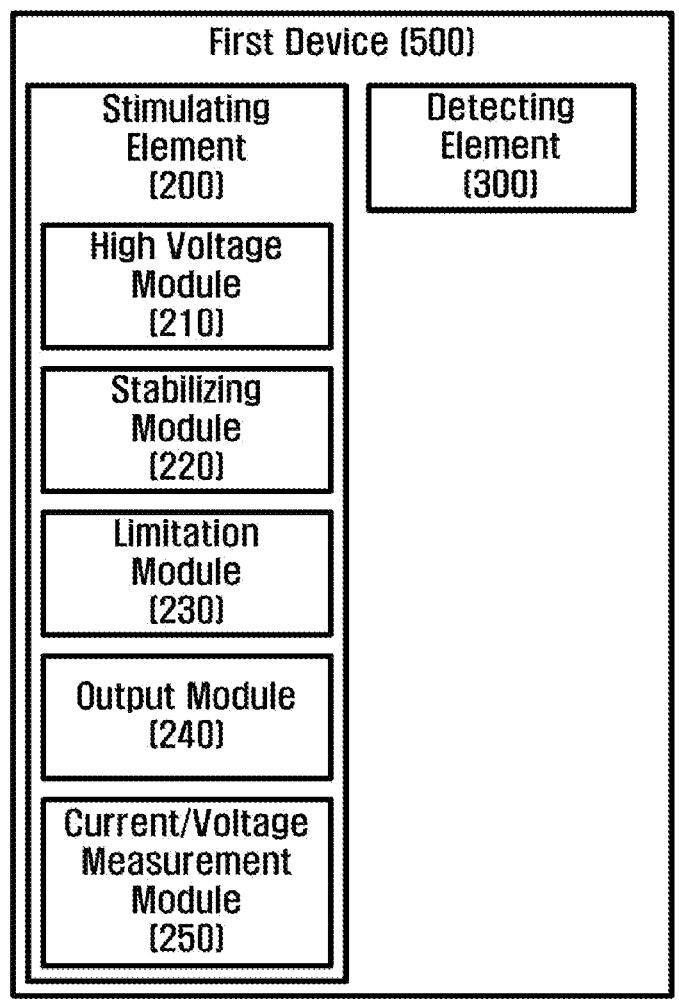
FIG. 13 and FIG. 14 are schematic block diagrams of a stimulating element and a detecting element of a first device, according to some embodiments.
Figure 14:
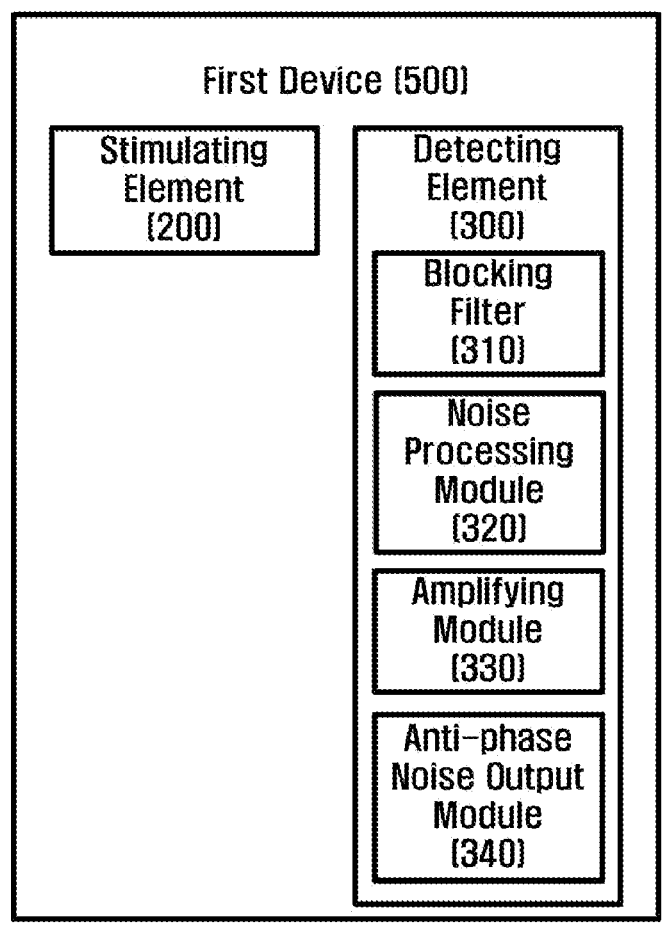

Detailed compositions of the stimulating element 200 and the detecting element 300 are presented hereafter referring to FIGS. 13 and 14.

FIGS. 5-8 are schematic cross sections of electrodes according to some embodiments. As some embodiments illustrated, electrodes are constituted with a first electrode 110 and a second electrode 120. A first electrode 110 and a second electrode 120 share a face contacting with a subject's skin or scalp, or the first electrode 110 and the second electrode 120 individually contact with the skin or scalp.

The first electrode 110 includes an electrolyte layer 111 directly contacting with the scalp and a conducting film 112 connected with one side of the electrolyte layer 111. The electrolyte layer 111 is either a solid electrolyte layer or a wet electrolyte layer, and the electrolyte layer 111 and the conducting film 112 are ductile and configured to be deformed to correspond to a curved surface of the scalp. In some embodiments, if the electrolyte layer 111 is the wet type, a first electrode 110 or second electrode 120 includes a waterproofed protective layer. In some another embodiments, a waterproofing process is directly applied to the first electrode 110 or the second electrode 120.

In some embodiments, the electrolyte layer 111 includes a hydrogel layer containing a gel-type electrolyte, and the conducting film 112 includes, but is not limited to, a ductile conductive fabric layer. The electrolyte layer 111 has any ductile form containing electrolyte, and likewise, the conducting layer 112 has any form, without limitation, if a conductor material of the conducting layer 112 is a ductile material that bends responding to a curve of the skin.

In some embodiments, the first electrode 110 comprises an electrolyte layer having an impedance value of 1 kΩ to 20 kΩ in the course of brain stimulating process, e.g., while the first electrode 110 supplies a minute electric current to stimulate the brain. That is, even if the electrolyte layer 111 is not a solid electrolyte layer, the system is constituted inasmuch as an impedance value falls within a corresponding range to the range of the impedance value.

In some embodiments, the second electrode 120 comprises a circuit board 121, a sensing electrode 122 formed on the circuit board 121, a sensing circuit 123 connected with the sensing electrode 122, and a detection filter 124.

Figure 5:
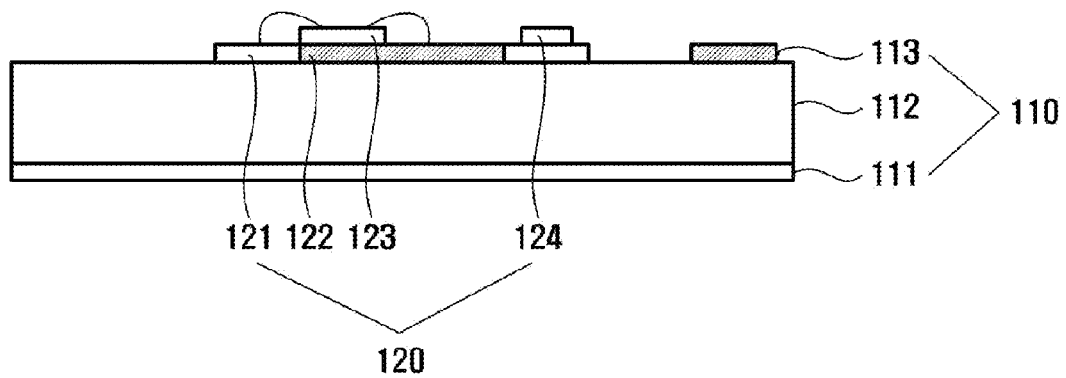
FIG. 5 is a schematic cross section of an electrode according to some embodiments.
Figure 6:
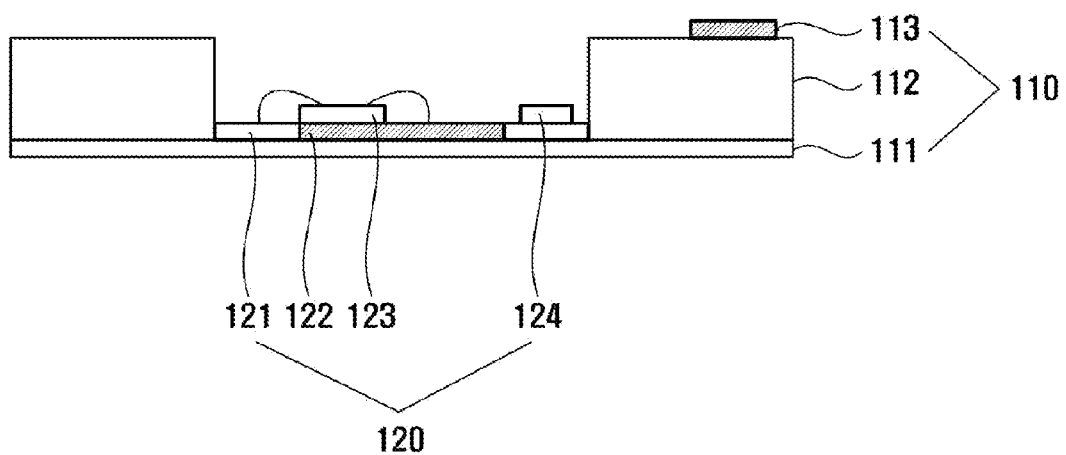
FIG. 6 is a schematic cross section of an electrode according to some embodiments.
Figure 7:
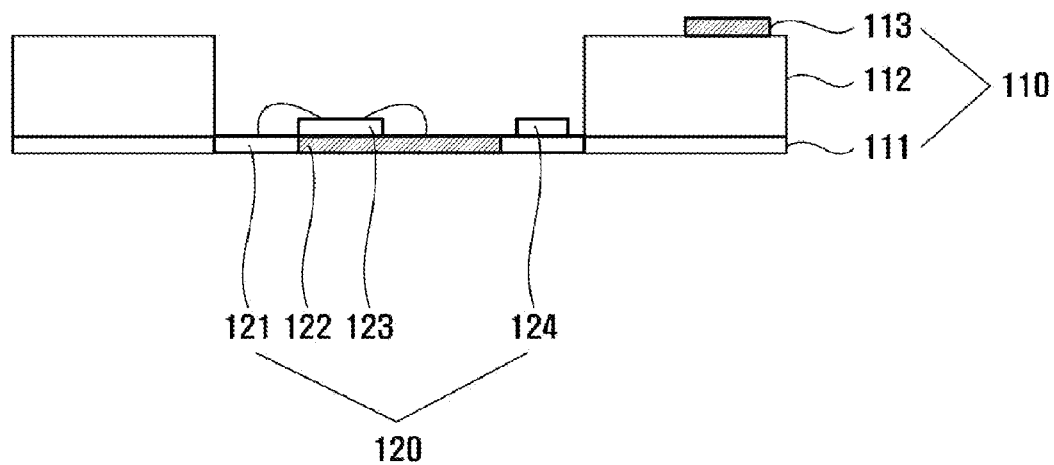
FIG. 7 is a schematic cross section of an electrode according to some embodiments.

In FIG. 5, the second electrode 120 is illustrated, but not limited to, being laminated on the upper side of the first electrode 110. The second electrode 120 is arranged on the inner side of the first electrode 110 as shown in FIG. 6, or both the first electrode 110 and the second electrode 120, both of which are exposed to the outer side, are simultaneously contacting with the skin, as shown in FIG. 7.

Figure 8:
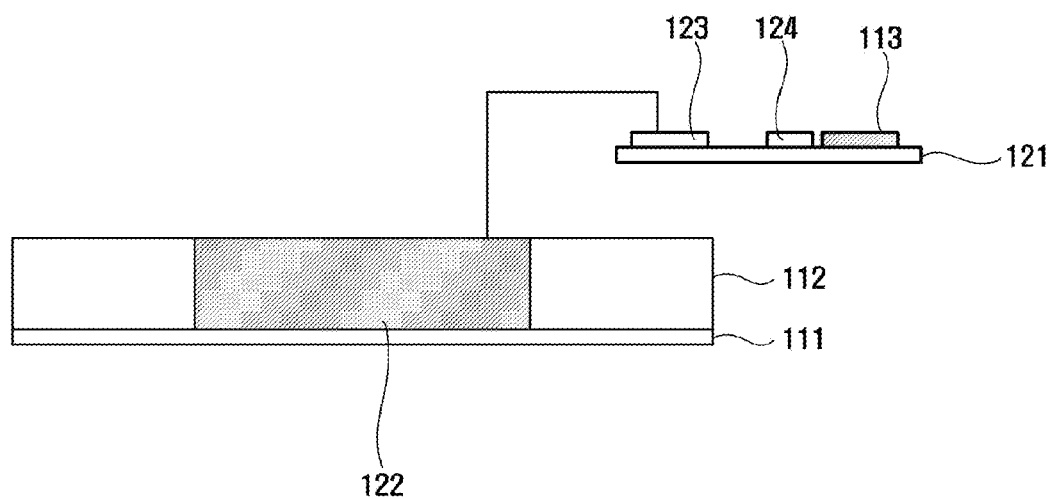
FIG. 8 is a schematic cross section of an electrode according to some embodiments.

Also, as shown in FIG. 8, only the sensing electrode 122 is built on the electrolyte layer 111, while the sensing circuit 123 connected with the sensing electrode 122 and the detection filter 124 are arranged on the circuit board 121.

Figure 9:
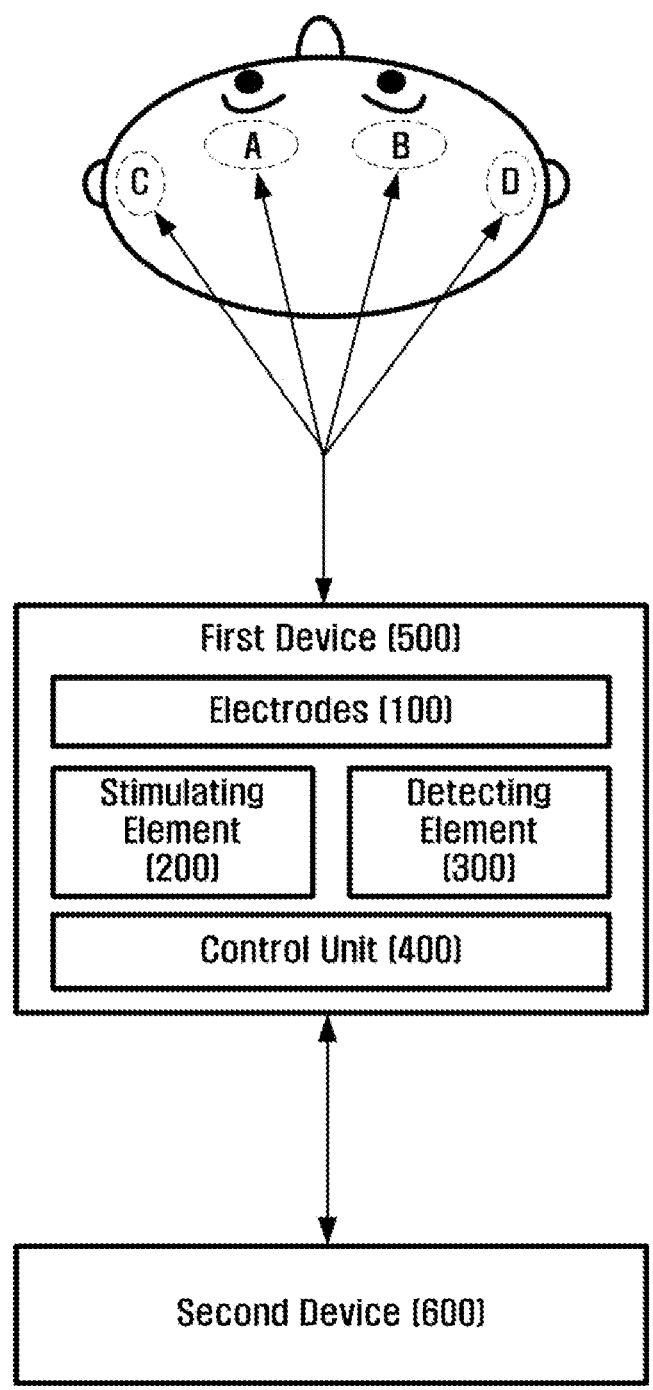
FIG. 9 is a schematic block diagram of a communication between devices of a brain stimulating system, according to some embodiments.
Figure 10:
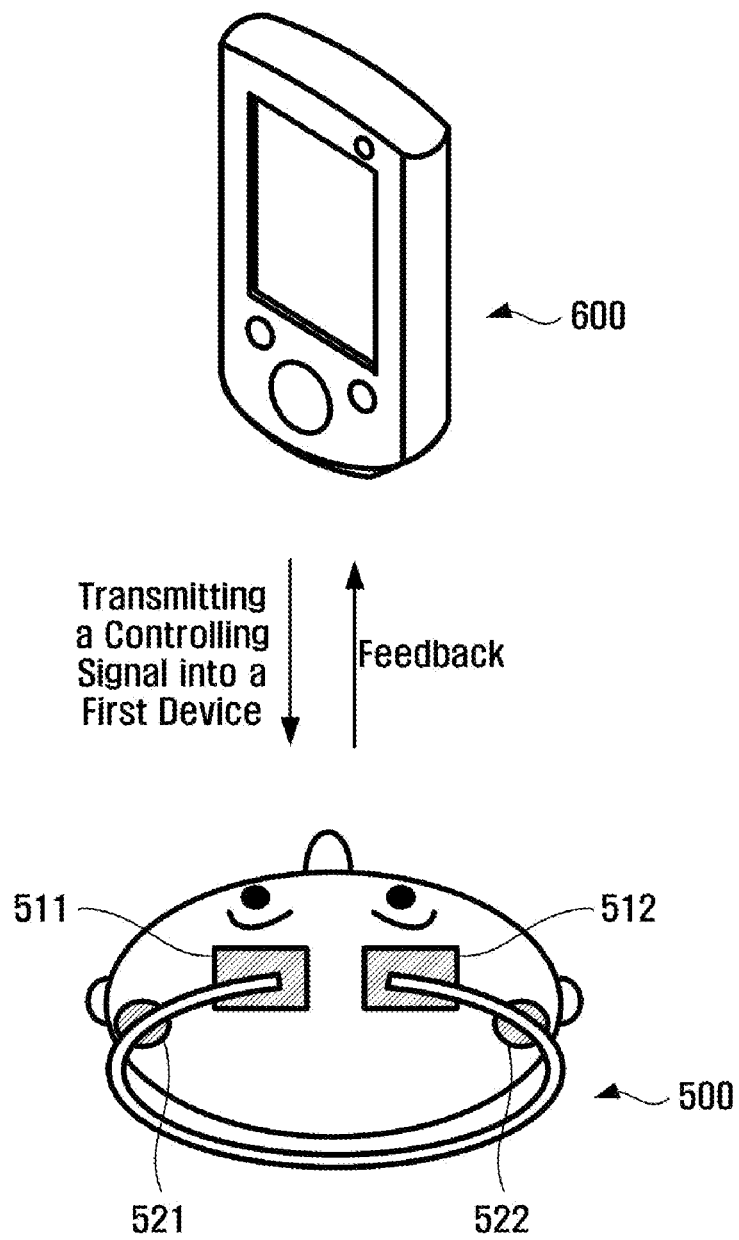
FIG. 10 is a schematic drawing that shows example embodiments of the system of FIG. 9.

FIG. 9 is a schematic block diagram of a communication between devices of a brain stimulating system, according to some embodiments, and FIG. 10 is a schematic drawing that shows example embodiments of the system of FIG. 9. A first electrode 100 comprises first sub-electrodes 511 and 512 arranged at frontal lobe areas A and B, respectively, that measure a first brain signal, for example, a first minute voltage. The first electrode 100 further comprises second sub-electrodes 521 and 522 arranged at areas, other than the frontal lobes, C and D, that measure a second brain signal, for example, a second minute voltage. For instance, the brain stimulating system according to some embodiments performs a brain signal detection and a brain stimulation with the areas A and B on the frontal lobes, and performs a reference voltage detection with the areas C and D in vicinities of ears. Since not only a voltage generated from the brain by the brain signal (the first brain signal) but also an ordinary noise voltage (the second brain signal) flows in a body of a subject, a noise voltage is detected by reference electrodes.

The brain stimulating system according to some embodiments further comprises a control unit 400 configured to receive the first brain signal and the second signal, and the control unit 400 extracts a third brain signal from the difference between the first signal and the second signal. That is, the control unit 400 measures the amount of a minute electric current generated by the brain signal based on the second brain signal measured at the other areas (in the vicinities of the ears) wherein the first brain signal measured at the frontal lobes have little or no influence on the second brain signal, and based on these results, brain signals may be precisely extracted.

The electrodes 100 as such descriptions above controls the minute electric current generated through a stimulating element 200 based on calculated brain signals as such methods above.

As shown in FIG. 9, the brain stimulating system according to some embodiments includes the stimulating element 200, a first device 500 that, comprising a detecting element 300, directly contacts with the brain areas, and a second device 600 that comprises a control unit that receives data containing the brain signal from the first device 500 and manages the received data.

As shown in FIG. 10, in some embodiments, the first device 500 is a headset to be worn on a head, and the second device 600 is any type of a terminal device which communicates with a mobile device or the first device 500. Based on brain signals, the first device 500 or the second device 600 controls the minute electric current. That is, the first device 500 analyzes, by itself, brain signals and controls the minute electric current automatically or manually, or the brain signals are sent to the second device 600 and be analyzed at the second device 600 so that signals that control the minute electric current are generated, and these signals are sent to the first device 500 again to be controlled.

Figure 11:
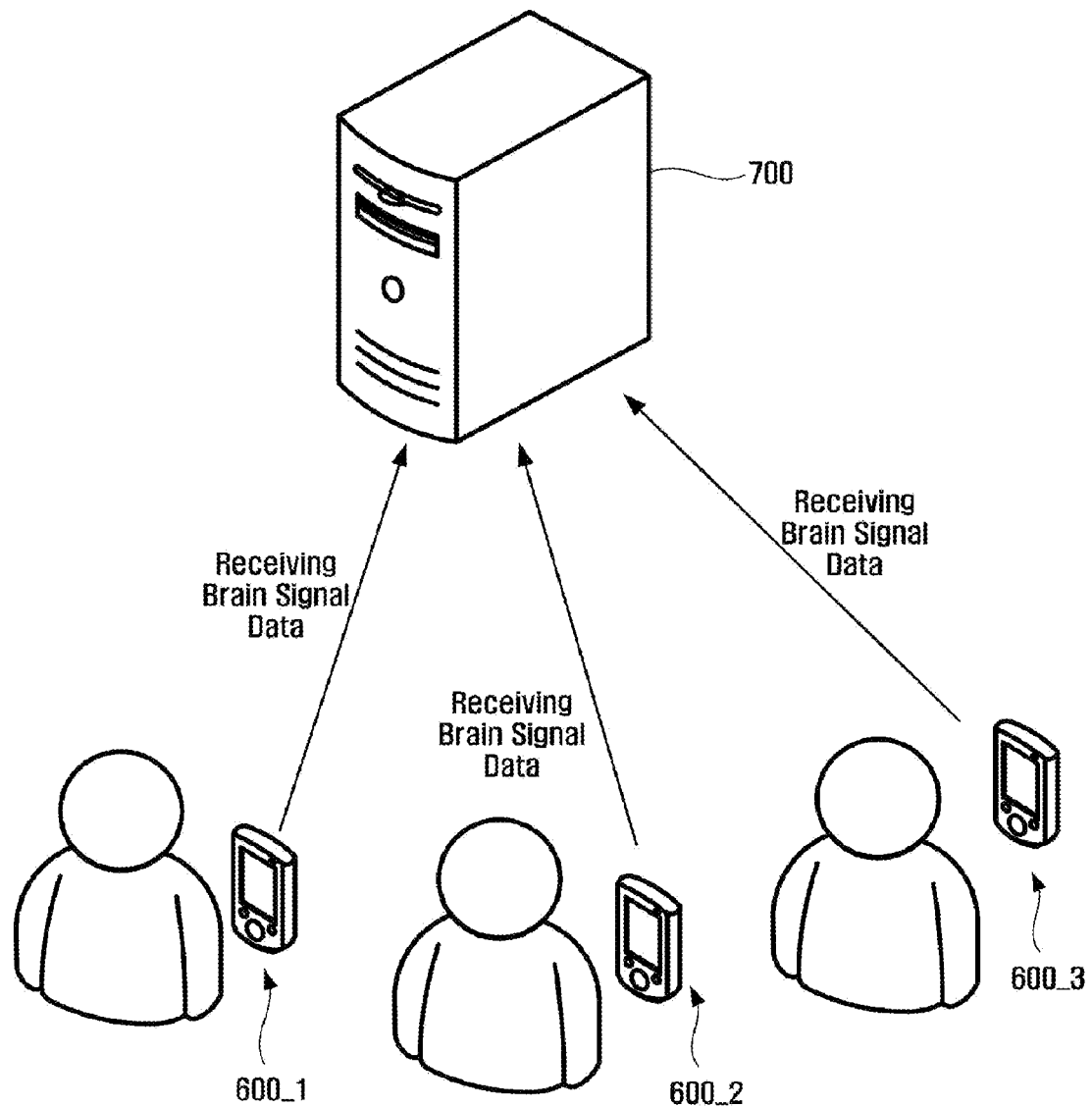
FIG. 11 is a schematic block diagram of a data collection structure of a brain stimulating system, according to some embodiments.

FIG. 11 is a schematic block diagram of a collection structure of data of a brain signal of a brain stimulating system, according to some embodiments. Referring to FIG. 11, a block diagram is shown that illustrates a collection structure of plural data of a brain stimulating system according to some embodiments. The system comprises a server 700 that communicates with a first device 500 or one of second devices 600_1, 600_2 and 600_3 and receives brain signals and manages a plural number of measured data. The server 700 analyzes a brain signal states of a group of users, based on brain signals received from devices 600_1, 600_2 and 600_3 of a plural number of users in the same time zone. To synchronize the received brain signals, brain signals or a time stamp to reference signal is used.

In some embodiments, the server 700 includes a control unit that runs a minute electric current algorithm and transmits a control signal of the minute electric current drawn from the minute electric current algorithm into the first device 500 or the one of second devices 600_1, 600_2 and 600_3. On this wise, the server 700 achieves an anticipated effect by controlling multiple devices according to the brain signal states of the group of users.

Figure 12:
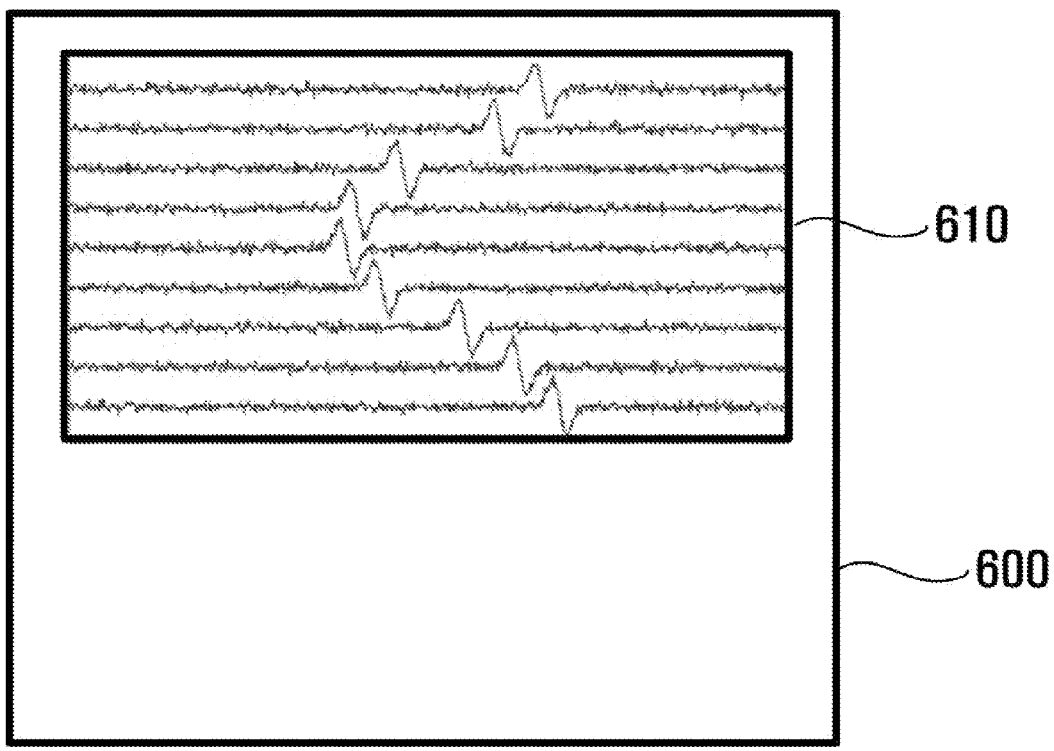
FIG. 12 is a schematic structure of a monitoring element of a brain signal, according to some embodiments.

FIG. 12 is a schematic structure of a monitoring element of a brain signal, according to some embodiments. Referring to FIG. 12, a second device 600 further contains a monitoring element 610 that presents brain signals or brain activity indices calculated from the monitoring element 610. The shown example shows the monitoring element 610 arranged at the second device 600, but it is not limited to this. In some other embodiments, the monitoring element 610 arranged at the first device 500 of FIG. 9. The brain activity indices are, for example, data that contains response analysis using the user's sensory evoked potential, concentration or various emotional states by band analysis of brain signal frequency, or types of brain signal.

In some embodiments, a user directly checks his or her brain signal states referring to such the monitoring element 610, and determines a proper stimulation strength or pattern by controlling a stimulating element 200 in real time in response to a result of the monitoring element 610.

FIGS. 13 and 14 are schematic block diagrams of a stimulating element 200 and a detecting element 300 of a first device, according to some embodiments.

The stimulating element 200 contains at least one of the following: a high voltage module 210, a stabilization module 220, a limitation module 230, an output module 240, or a current/voltage measurement module.

The high voltage module 210 generates an initial voltage current to stimulate a frontal lobe of a subject, wherein the initial voltage current has a feature of voltage under 20V or under a few mA, but it is not limited to this.

The stabilization module 220 stabilizes the initial voltage current, for instance, the stabilization module 220 transforms the initial voltage current into a minute electric current, but it is not limited to this, and the transforming process is performed at an output module 240 described later, while the transformation process of the minute electric current is skipped.

The limitation module 230 compares a current value detected at the current/voltage measurement module 250 with a predetermined value of an overcurrent, and then blocks an output of electric stimulation signals if the current value is greater than the predetermined value. Thus, the limitation module 230 blocks a deliverance of electric stimulation signal greater than a proper level of stimulation to user's brain.

The output module 240 is supplied with electric current from the stabilization module 220 and outputs predetermined voltage or current.

The current/voltage measurement module 250 measures a voltage or current value that is put out from the output module 240 in real time, and the current/voltage measurement module 250 monitors an output status, and the current/voltage measurement module 250 controls a minute electric current delivered to a current user via a display element.

The detecting element 300 comprises one or more of the followings: a blocking filter 310 that blocks a minute electric current generated at a stimulating element 200, a noise processing module 320 that separates common noise from at least one brain signal, an amplifying module 330 that amplifies brain signals from which noise is removed, or an anti-phase noise output module 340 that offsets noise flowing on the scalp of a subject. A blocking filter 310 is a DC blocking filter if brain stimulation is performed with a direct current. However, in some embodiments, the blocking filter 310 is a software filter (implemented by, e.g., a processor) that receives brain stimulating signals and removes the received brain stimulating signals from brain signals if the received brain stimulating signals perform brain stimulation with alternating a current or a pulsed current having the same frequency range as detected brain signals. The noise processing module 320 separates a common noise component existent in common among detected brain signals of at least one electrode of electrodes 100 and/or the detecting element 300, and removes the separated signals from each brain signal.

The amplifying module amplifies amplitude so as to easily detect brain signals from which noise is removed.

The anti-phase noise output module 340 changes the phase of noise vibration and output the changed noise vibration via at least one detecting electrode so that a common noise component extracted from the noise process module 320 is decreased or offset on the scalp of the subject.

In concluding the detailed description, those skilled in the art will appreciate that many variations and modifications can be made to the preferred embodiments without substantially departing from the principles of the some embodiments described above. Therefore, the described some embodiments are used in a generic and descriptive sense only and not for purposes of limitation.

I claim:

1. A brain stimulating system, comprising:
a first electrode configured to supply a minute electric current to stimulate a brain, wherein the minute electric current is a direct current (DC); and
a second electrode configured to detect at least one brain signal received from the brain, wherein the second electrode comprises a blocking filter configured to block the minute electric current,
wherein the at least one brain signal comprises a DC component and an alternating current (AC) component, and
wherein the blocking filter is configured to block the DC component corresponding to the minute electric current supplied by the first electrode.

2. The system of claim 1, wherein the first electrode comprises an electrolyte layer having an impedance value of 1 kΩ to 20 kΩ while the first electrode supplies the minute electric current to stimulate the brain.

3. The system of claim 1, wherein the first electrode comprises: a solid electrolyte layer configured to be directly contacted with the scalp covering the brain, and a conducting film connected with one side of the solid electrolyte layer.

4. The system of claim 3, wherein the solid electrolyte layer and the conducting film are ductile and configured to be deformed to correspond to a curved surface of the scalp.

5. The system of claim 1, wherein the first electrode comprises a wet electrolyte layer directly contacted with the scalp, and at least one of the first electrode or the second electrode contains a waterproofed protective layer.

6. The system of claim 1, wherein the first electrode comprises:
a first sub-electrode configured to be arranged at a frontal lobe area of the brain to detect a first brain signal responsive to the minute electric current; and
a second sub-electrode configured to be arranged at an area other than the frontal lobe area to detect a second brain signal responsive to the minute electric current.

7. The system of claim 6, the system further comprises a control unit configured to receive the first brain signal and the second brain signal, and extract a third brain signal from a difference between the first brain signal and the second brain signal.

8. The system of claim 1, the system further comprises a control unit configured to control the minute electric current supplied by the first electrode based on the at least one brain signal.

9. A brain stimulating system, comprising:
a first electrode configured to
supply a minute electric current to stimulate a brain, wherein the minute electric current has one of one or more frequency values predetermined based on a user input, and
detect at least one brain signal received from the brain;
a stimulating element configured to control the minute electric current, the stimulating element connected with the first electrode; and
a detecting element configured to receive the at least one brain signal, the detecting element connected with the first electrode,
wherein the detecting element comprises a blocking filter configured to block one or more components of the at least one brain signal, the one or more components have the same frequency value as the one of one or more frequency values predetermined based on the user input.

10. The system of claim 9, wherein the first electrode comprises an electrolyte layer having an impedance value of 1 kΩ to 20 kΩ while the first electrode supplies the minute electric current to stimulate the brain.

11. The system of claim 9, wherein the first electrode comprises: a solid electrolyte layer configured to be directly contacted with the scalp covering the brain, and a conducting film connected with one side of the solid electrolyte layer.

12. The system of claim 11, wherein the solid electrolyte layer and the conducting film are ductile and configured to be deformed to correspond to a curved surface of the scalp.

13. The system of claim 9, wherein the first electrode comprises a wet electrolyte layer directly contacted with the scalp, and at least one of the first electrode or the second electrode contains a waterproofed protective layer.

14. The system of claim 9, wherein the first electrode comprises:
a first sub-electrode configured to be arranged at a frontal lobe area of the brain to detect a first brain signal responsive to the minute electric current; and
a second sub-electrode configured to be arranged at an area other than the frontal lobe area to detect a second brain signal responsive to the minute electric current.

15. The system of claim 14, the system further comprises a control unit configured to receive the first brain signal and the second brain signal, and extract a third brain signal from a difference between the first brain signal and the second brain signal.

16. The system of claim 9, the system further comprises a control unit configured to control the minute electric current supplied by the first electrode based on the at least one brain signal.

17. A brain stimulating system, comprising:
a first device comprising a stimulating element configured to generate a first minute electric current to stimulate a brain and a detecting element configured to measure at least one brain signal received from the brain; and
a second device comprising a control unit configured to receive data containing the at least one brain signal from the first device and manage the received data,
wherein the first device is configured to
analyze a current status of a user,
determine a range of a stimulation magnitude for the user, based on the analyzed status,
generate a second minute electric current corresponding to the determined range, and
stimulate the brain by using the generated second minute electric current, and
wherein the detecting element comprises a blocking filter configured to block the minute electric current and an anti-phase noise output module configured to change a phase of noise vibration, and output the changed noise vibration.

18. The system of claim 17, wherein at least one of the first device or the second device is configured to control the minute electric current based on the at least one brain signal.

19. The system of claim 17, the system further comprises a server configured to communicate with at least one of the first device or the second device, receive the at least one brain signal, and manage the data.

20. The system of claim 19, wherein the server is configured to analyze brain signal states of a group of users based on the corresponding at least one brain signal.

21. The system of claim 19, wherein the server is configured to transmit a control signal of the minute electric current, corresponding to brain signal states of a group of users, to at least one of the first device or the second device.

* * * * *